United States Patent [19]

Guidotti et al.

[11] Patent Number: 5,709,715

[45] Date of Patent: Jan. 20, 1998

[54] SILICON OR SILICA SUBSTRATE WITH A MODIFIED SURFACE, PROCESS FOR PRODUCING THE SAME, NEW ORTHOESTERS AND PROCESS FOR PRODUCING THE SAME

[75] Inventors: Bruno Guidotti, Freienbach; Walter Caseri; Ulrich Suter, both of Zürich; Wolfgang Saur, Buttikon, all of Switzerland

[73] Assignee: Owens-Corning Fiberglas Technology Inc., Summit, Ill.

[21] Appl. No.: 211,191

[22] PCT Filed: Jul. 6, 1993

[86] PCT No.: PCT/CH93/00173

§ 371 Date: May 19, 1994

§ 102(e) Date: May 19, 1994

[87] PCT Pub. No.: WO94/02425

PCT Pub. Date: Feb. 3, 1994

[30] Foreign Application Priority Data

Jul. 23, 1992 [CH] Switzerland ............................ 2327/92
Jun. 2, 1993 [CH] Switzerland ............................ 1644/93

[51] Int. Cl.$^6$ .................. C03C 17/28; C04B 41/46; C07C 69/54

[52] U.S. Cl. .................. 8/115.51; 8/120; 428/404; 428/405; 428/543; 428/446; 428/406; 428/409; 428/365; 428/428; 428/429; 427/389.8; 427/385.5; 427/389.7; 427/386; 427/331; 427/389.9; 427/299; 568/595; 549/560

[58] Field of Search .................. 8/115.51, 120; 252/8.6, 8.7, 8.75, 8.8, 8.9, 8.83, 8.91, 8.81, 8.84; 428/404, 405, 543, 446, 406, 409, 365, 428, 429; 427/389.8, 385.5, 389.7, 386, 389.9, 331, 299; 568/595; 549/560

[56] References Cited

U.S. PATENT DOCUMENTS

| | | | |
|---|---|---|---|
| 3,515,693 | 6/1970 | Wood | 524/109 |
| 3,637,458 | 1/1972 | Parrish | 428/314.2 |
| 3,823,794 | 7/1974 | Bre | 181/286 |
| 4,107,140 | 8/1978 | Blount | 521/154 |
| 4,243,605 | 1/1981 | Eisenhardt, Jr. et al. | 556/514 |
| 4,657,815 | 4/1987 | Goel et al. | 428/403 |
| 4,778,987 | 10/1988 | Saaski et al. | 250/226 |
| 4,900,807 | 2/1990 | Nishikawa et al. | 528/362 |
| 5,006,410 | 4/1991 | Viola et al. | 428/411.1 |

FOREIGN PATENT DOCUMENTS

| | | |
|---|---|---|
| 4-56857 | 2/1992 | Japan. |
| 2029433 | 3/1980 | United Kingdom. |

*Primary Examiner*—Alan Diamond
*Attorney, Agent, or Firm*—C. Michael Gegenheimer; Inger H. Eckert

[57] ABSTRACT

The silicon or silica substrates described have a modified surface of a new type occupied by the alcohol fraction of an orthoester. The alcohol fraction may be saturated or unsaturated. The surface of the substrate is modified by being treated with an orthoester, the water being eliminated from the surface by hydrolysis and then replaced by the resulting alcohol or silylether. Besides many other compounds, new orthoesters having the formula $R^1C[OCH_2—CH_2—O—CO—CH=CH_2]_3$, in which $R^1$ stands for hydrogen or for a clearable organic residue, R stands for $(CH_2)_n$, in which n stands for an integer between 1 and 18, and new orthoesters having the formula (I), are particularly appropriate. In the formula (I), $R^1$ stands for hydrogen or an organic residue, $R^3$ stands for hydrogen or an alkyl group with 1 to 6 carbon atoms; and $R^4$ stands for hydrogen, an alkyl group or an alkyl group or a phenyl group. The modified surfaces have a larger wetting or contact angle, and thus a reduced wettability. In addition, they are capable of reacting with other monomers or polymers by means of all sorts of reactive substituents. This kind of surface modification advantageously replaces the silanization which was up to now usual for glass and other silicates.

62 Claims, No Drawings

SILICON OR SILICA SUBSTRATE WITH A MODIFIED SURFACE, PROCESS FOR PRODUCING THE SAME, NEW ORTHOESTERS AND PROCESS FOR PRODUCING THE SAME

This application is a 371 of PCT/CH93/00173 filed Jul. 6, 1993.

The invention refers to a silicon or silicon dioxide substrate with a modified surface and to processes for producing the same, as well as to new orthoesters and methods for preparing the same.

The modification of surfaces of silicon and silicon dioxide substrates in particular in connection with the development of adhesives or adhesion promotors for such substrates, particularly for glass, so far was generally based on the idea that the silicon and silicon dioxide surfaces, respectively, are covered by silanol groups and water. Thus, so far, in the majority of cases such compounds as chloro silanes or alkoxy silanes were used for modifying silicon and silicon dioxide surfaces, respectively, inasmuch that it was thought that they do react with the silanol groups and do form covalent bonds therewith. Accordingly, this method was called "silanization".

Now, the basis of the present invention is the finding that the hydroxyl groups present on the surface of such a substrate, e.g. on a glass surface, at least partially form part of water which is molecularly bonded to the silicon dioxide surface.

Thus, it is the object of the present invention to provide silicon and silicon dioxide substrates, which are modified in a novel manner with organic compounds, have novel properties, and are particularly useful as a basis for anchoring of organic polymers.

Now, said novel silicon and silicon dioxide substrates, having a modified surface, are characterized in that their surface is occupied by an alcohol or a silylether.

Such a modified surface shows an essentially increased boundary or contact angle for water, as compared with corresponding non-modified surfaces. Thus, the wettability for water is reduced, whereas the wettability for many organic compounds is increased.

In the method for preparing such modified substrates according to the present invention the surfaces to be modified are treated with an orthoester.

As is generally known, the term "orthoester" stands for the aliphatic and aromatic esters of the corresponding orthocarbonic acids, which are not known to exist in free form, thus compounds of the type $R^1—C[OR^2]_3$.

According to the actual status of knowledge it is assumed that, on treating the surface of silicon or silicon dioxide substrate, an alcohol is formed from the orthoester. Thereby, the water is eliminated by hydrolysis from said surface, and the alcohol or silylether formed thereafter take the place of the eliminated water.

Schematically this may be represented as follows:

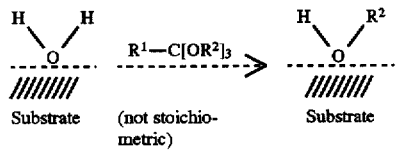

Examples of the manifold field of applications of the new technology are summarized in Table 1 hereafter.

Among the applications listed there, the method according to the present invention is particularly useful for modifying the surfaces of glass, quartz, silicon or silicon covered with silicon dioxide. Preferred applications are e.g. the modification of pyrogenic silicic acid, glass panes, wafers and oxidized wafers.

By such a treatment, e.g., the adherence of many plastics on the substrate can be essentially improved in an inexpensive manner. In particular, it allows to directly polymerize onto the substrate adhesives and coating materials, and polymeric interlayers for a later chemical reaction with adhesives and coating materials.

TABLE 1

| Product group/products | Applications | Utilities |
|---|---|---|
| 1 Silicate fillers | | |
| 11 Pyrogenic silicic acid | Hydrophobizing Surface coating | Adhesives Sealants Plastics Coatings Lacquers Colors Molding compounds |
| 12 Precipitated silicic acid | Hydrophobizing Surface coating | Adhesives Sealants Plastics Coatings Lacquers Colors Molding compounds |
| 13 Silica gels | Hydrophobizing Surface coating | Catalysts Siccatives chromatographic substrates |
| 14 Quartz powder | Hydrophobizing Surface coating | Adhesives Sealants Plastics Coatings Lacquers Colors Molding compounds |
| 15 Glass powder | Hydrophobizing Surface coating | Dental products Molding compounds Composites |
| 16 Various silicates | Hydrophobizing Surface coating | Zeolites |
| 2 Fibers and textiles | | |
| 21 Glass fibers | Hydrophobizing Finishing Adhesion promotion | Composites Glass fiber reinforced plastics Telecomunication Measuring technique |
| 22 Glass textiles | Hydrophobizing Finishing Adhesion promotion | Electro laminates Composites Glass fiber reinforced plastics Industrial protection clothing |
| 23 Glass wool/rock wool | Hydrophobizing | Insulating materials Building materials |
| 3 Flat glasses | | |
| 31 Window glass composites (including insulating glass systems) | Hydrophobizing Adhesion promotion Surface coating Corrosion protection | Insulating glass windows Security glass composites Motor car glass |
| 32 Optical glasses | Hydrophobizing Adhesion promotion Surface coating Corrosion protection | Optical measuring technique Screens Photography |
| 33 Glass membranes | Hydrophobizing Adhesion promo- | Chemical measuring technique |

TABLE 1-continued

| Product group/products | Applications | Utilities |
|---|---|---|
| | tion<br>Corrosion pro-<br>tion | Surface coating<br>Biotechnology<br>Chemical Engineer-<br>ing |
| 4 Special Silicates | | |
| 41 Silicon wafers for electronic and solar technique | Hydrophobizing<br>Surface coating<br>Corrosion pro-<br>tection | |
| 42 Aerogel glasses | Hydrophobizing<br>Surface coating<br>Corrosion pro-<br>tection | Technical insula-<br>ting layers<br>Light glass for<br>vehicles |

"Aerogels" are newly developed materials of the silicate research, having the form of transparent, glass-like bodies, e.g. plates, and a specific gravity of 0.05 to 0.1 g/cm$^3$. So far, they were not industrially used, which is thought to be due to their poor resistance against hydrolysis. This drawback can be avoided by treating them with orthoesters according to the present invention.

Silanes cannot be used for hydrophobicity coating wafers, since from their preparation they always contain traces of chlorine. However, chlorine is a strong poison for wafers. Contrary to this, the preparation of orthoesters can be effected by methods which do not use chlorine.

The modification of surfaces of silicon and silicon dioxide substrates according to the present invention shows a number of advantages, as compared with the use of silanes, i.e.:

The preparation of orthoesters is considerably less expensive than the preparation of silanes, since it rests on an organic raw material basis, i.e. on petroleum, and thus in general is energetically much more favorable than the preparation of organic silicon compounds.

They can be prepared by simpler methods, without the use of chlorine chemistry, i.e. in a way which is safer and less harmful to the environment.

At least for simple orthoesters, their use is physiologically safe.

Results which are clearer and analytically more easily assertainable are obtained, particularly for coatings.

There is a wide variety of methods for preparing orthoesters which are tailor-made for their specific use thus providing the possibility of preparing new or more suitable coatings.

Since, with respect to hydrolysis, the C—O bond is generally more stable than the Si—O bond, more resistent bonding coats over the organic alcohol adducts late obained as well.

The alcohol moiety of said orthoesters can comprise a hydrocarbon moiety, the sequence of which may be interrupted by hetro atoms, in particular oxygen. Also, an aromatic alcohol moiety may be substituted. In particular, the alcohol moiety may be epoxidized, i.e. it may derive from glycidyl alcohols.

Prefered are alcohol moieties which either are unsaturated or epoxidized. Thereby, substrate sufaces are obtained which may be further reacted by radicalic polymerization or polyaddition with other compounds.

The following orthoesters of the general formula $$R^1-C[OR^2]_3$$

proved to be particularly suitable for the purposes of the present invention:

1. Trimethyl orthoformate
   = orthoformic acid methylester
   = trimethoxymethane
   $R^1 = H$   $R^2 = CH_3$
2. Trimethyl orthoacetate
   = orthoacetic acid ethylester
   = trimethoxyethane
   $R^1 = CH_3$   $R^2 = CH_3$
3. Triethyl orthoformate
   = orthoformic acid ethylester
   = triethoxymethane
   $R^1 = H$   $R^2 = CH_2-CH_3$
4. Triethyl orthoacetate
   = orthoacetic acid ethylester
   = triethoxyethane
   $R^1 = CH_3$   $R^2 = CH_2-CH_3$
5. Tributyl orthoformate
   = orthoformic acid butylester
   = tributoxymethane
   $R^1 = H$   $R^2 = CH_2-CH_2-CH_2-CH_3$
6. Triethyl orthovalerate
   = orthovaleric acid ethylester
   = triethoxypentane
   $R^1 = [CH_2]_3-CH_2$   $R^2 = CH_2-CH_3$
7. Triallyl orthoformate
   = orthoformic acid allylester
   = triallyloxymethane
   $R^1 = H$   $R^2 = CH_2-CH-CH_2$
8. Tri(ethylacrylate) orthoformate
   = orthoformic acid(ethylacrylate)ester
   = tri(ethoxyacrylate)methane
   $R^1 = H$   $R^2 = CH_2-CH_2-O-CO-CH=CH_2$ The lastmentioned compound 8 belongs to a first group of new orthoesters, i.e. orthoesters of the gneral formula $$R^1C[OR^2-O-CO-CH=CH_2]_3 \quad (1),$$

wherein $R^1$ is hydrogen or an organic residue, and $R^2$ is $(CH_2)_n$, n being an integer from 1 to 18.

The new orthoesters of formula (1) are prepared according to the present invention by reacting an acid amide of the general formula $$R^1-CO-NH_2 \quad (2)$$

with benzamide and the corresponding (2-hydroxyalkyl)-acrylate. Preferably, the reaction is carried through as a one-pot reaction.

Furthermore, particularly suitable are orthoesters the alcohol moieties of which derive from the following glycidyl alcohols:

2,3-Epoxy-2-methyl-3-phenyl-1-propanol = 2-methyl-3-phenylglycidol

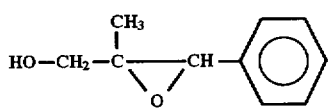

(corresponding to orthoester 9)

2,3-Epoxy-2-methyl-1-propanol

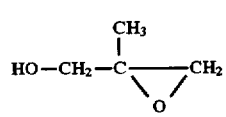

(corresponding to orthoester 10)

2,3-Epoxy-1-propanol

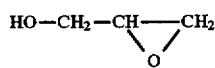

(corresponding to orthoester 11)

The orthoesters 9 to 11 belong to a second group of new orthoesters according to the present invention, i.e. orthoesters of the general formula

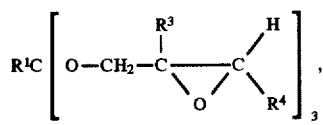

wherein:

$R^1$ is hydrogen or an organic residue;

$R^3$ is hydrogen or an alkyl group of 1 to 6 carbon atoms; and $R^4$ is hydrogen, an alkyl group or a phenyl group.

According to the present invention, the orthoesters of the general formula (4) are prepared by transesterification of an orthoester of the general formula

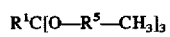

wherein $R^5$ is $(CH_2)_m$, m being an integer from 0 to 5, with an alcohol of the general formula

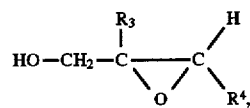

Other suitable orthoesters are described in the publication of *Robert H. DeWolfe*, Carboxylic Ortho Acid Derivatives, Academic Press 1970 (Organic Chemistry Series Monographs No. 14).

For the treatment of the substrate with said orthoesters, the substrate is preferably pre-dried, e.g. at 150° C./1 to 3 mbar. The application of the orthoesters is preferably effected at room temperature, this particularly for acrylic compounds, or under reflux, or in the gas phase.

If the alcohol moiety of the orthoester is unsaturated or epoxidized, the modified surface may be reacted further with other reactive compounds.

In this way, either an adhesive layer or a coating compound can be directly anchored on the surface of the modified substrate (cf. compounds of group 1 hereafter);

or a polymeric layer comprising active hydrogen atoms can be formed on the surface of the modified substrate, which is thereafter further reacted with an adhesive or a coating compound which is able to form chemical bonds with said reactive hydrogen atoms (cf. compounds of group 2 hereafter).

Examples of suitable compounds for said further reaction with unsaturated alcohol moieties are:

1 Unsaturated compounds without active hydrogen atoms, particularly:
1.1 Monomers having at least one olefinic double bond;
1.2 Alkylacrylates and/or alkylmethacrylates;
1.3 Styrene and/or acrylonitrile;
2 Unsaturated compounds having active hydrogen atoms, particularly:

2.1 Compounds of the general formula

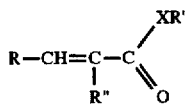

wherein:

R and R' independently from each other are a hydrogen atom or a substituent having at least one active hydrogen atom; and R" is a hydrogen atom or a substituent having at least one active hydrogen atom or a lower alkyl group or CN;

X is an oxgen or sulfur atom or the residue NH; e.g.:

2.1.1 acrylic acid;
2.1.2 2-hydroxyethylacrylate;
2.1.3 4-hydroxybutylacrylate;
2.1.4 2,3-dihydroxypropylacrylate; =glycerylmonoacrylate;
2.1.5 2,3-dihydroxypropylmethacrylate =glycerylmonomethacrylate;
2.1.6 hydroxypropylmethacrylate; or
2.1.7 acrylamide;

2.2 Compounds of the general formula

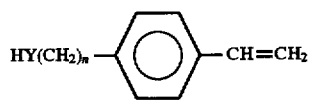

wherein:

n is an integer from 0 to 18; and

Y is an oxygen or sulfur atom or one of the residues NH, COO and $SO_3$; e.g.:

2.2.1 4-hydroxystyrene; or
2.2.2 4-aminostyrene;

2.3 Unsaturated dicarbonic acids and/or their anhydrides; e.g.:

2.3.1 maleic acid and/or maleic anhydride;
2.4 Epoxyacrylates and/or epoxymethacrylates; e.g.:
2.4.1 2,3-epoxypropylacrylate; or
2.4.2 2,3-epoxypropylmethacrylate.

The classes of compounds mentioned above can be combined at will, i.e. each molecule of the treated substrate can be reacted further with each of the said classes of compounds.

Preferably, the reaction of said unsaturated compounds with an unsaturated alcohol fixed on the substrate is effected by radicalic polymerization in the presence of azoisobutyric nitrile or dibenzoylperoxide as radical former.

Upon the further reaction of the modified surfaces with said reactive compounds, a polymer which is firmly anchored on the surface of the silicon dioxide substrate is obtained.

Particularly suitable for the further reaction of modified surfaces which are occupied by epoxidized alcohols are epoxy compounds and isocyanates.

EXAMPLE 1

Synthesis of Triallylorthoformate=Orthoformic Acid Allylester=Triallyloxymethane (Compound 7)

140.5 g (1 mole) of benzoylchloride was dropwise added within 20 minutes to a stirred and cooled mixture of 45 g (1 mole) of formamide, 174 g (3 mole) of allylalcohol and 200 ml of petroleum ether. The solution was stirred for 1 hour at 35° C., and the formed ammonium chloride and the formed benzoic acid were filtered off. The filtrate was dropwise added to 500 ml of a cooled and stirred sodium hydroxide solution. The organic phase was separated in a separating funnel, washed with 50 ml of water and dried overnight over CaH$_2$.

Yield: 123.7 g (61% of theory)

| $^1$H—NMR: | s | 5.30 ppm (1 H) | $^{13}$C—NMR: | 111.53 ppm |
|---|---|---|---|---|
| | dxt | 4.12 ppm (6 H) | | 65.13 ppm |
| | dxdxt | 5.93 ppm (3 H) | | 134.05 ppm |
| | dxdxt | 5.18 ppm | | 116.98 ppm |
| | dxdxt | 5.31 ppm (3 H) | | |

EXAMPLE 2

Synthesis of triglycidylorthoformate (Compound 11)

30 mg of p-toluenesulfonic acid monohydrate, dissolved in 1 ml of methanol, were added to a mixture of 3.15 g (0.297 mole) of trimethylorthoformate (compound 1—b.p.75=44° C.) and 106.5 g (1.44 mol) of glycidol (b.p.0.006=26° C.).

The reaction mixture was heated to 110° C., so that the clear solution simmered. Thereby, during about 1 hour about 12 ml (0.3 mole) of formed methanol distilled off through a Vigreux column (10 cm). During the following 5 hours the pressure was slowly but continuously reduced to 100 mbar by means of a water jet pump, in such a manner that the reaction mixture always simmered, but the vapor temperatur did not exceed the boiling temperature of methanol. For completing the reaction, boiling was continued for another 3 hours at 110° C. and 100 mbar (total reaction time: 9 hours). Altogether, about 28 ml (0.7 mol) of methanol could be separated.

After distilling off the excess of glycidol and by-products, 14.65 g (0.063 mole) of triglycidyl orthoformate in the form of clear, oily liquid were distilled off at 0.009 mbar and a vapour temperature of 138° C..

Analysis of triglycidyl orthoformate:

Yield: 14.65 g (21% of theory), B.P.0.07: 138° C., n$_D^{20}$: 1.463

| Microanalysis: | C | H | O |
|---|---|---|---|
| calculated: | 51.72% | 6.94% | 41.34% |
| fpound | 51.74% | 6.80% | 41.48% |

FT-IR (mesured as liquid film betweeen 2 salt plates)

| 3060 w, 3002 m | C—H st (epoxide) |
|---|---|
| 2932 m, 2888 m | C—H st (C—C—H) |
| 1483 w, 1458 w, 1428 w | —CH$_2$ delta |
| 1256 m | C—O—C st as (epoxide) |
| 1101 s, 1063 s | C—O—C st as (HC—O—CH$_2$) |

$^1$H-NMR (200 MHz, CDCl$_3$):

| delta (Ha) | = | 3.83 ppm |
| delta (Hb) | = | 3.83 ppm |
| delta (Hc) | = | 3.48 ppm |
| delta (Hd) | = | 3.13 ppm |
| delta (He) | = | 2.76 ppm |
| delta (Hf) | = | 2.58 ppm |

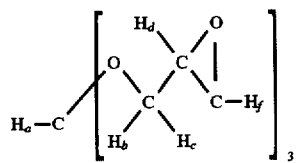

$^{13}$C-NMR (50 MHz; CDCl$_3$):

| delta (Ca) | = | 112 ppm |
| delta (Cb) | = | 65 ppm |
| delta (Cc) | = | 50 ppm |
| delta (Cd) | = | 44 ppm |

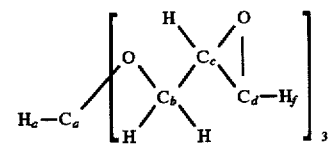

Remark:

Since the carbon atom C$_c$ is a chiral center, there are 2 pairs of enantiomers of triglycidyl orthoformate which show slightly different chemical shifts.

EXAMPLE 3

Treatment of Substrates with Orthoesters

Glass plates, silicon, silicon dioxide and Aerosil 200 were dried at 10$^{-2}$ mbar, dipped overnight into 2% solutions of ortho-ester in CCl$_4$, and refluxed overnight. In the case of Aerosil, the reaction products were analyzed by means of IR- and $^{13}$C-solid-NMR-spectroscopy, as well as by means of TGA (Thermogravimetric Analysis). The portion of organic product on Aerosil 200 typically was about 3% by weight.

The central carbon atoms of the orthoesters had disappeared in all cases from the $^{13}$C-NMR-spectrum; only the signals of the corresponding alcohols were visible.

For compounds of the general formula RC[OR']$_3$, wherein R=aryl and R'=alkyl, only C-H-vibrations of alkyl groups could be observed, whereas for R=alkyl and R'=aryl, only signals of aromatic C-H-stretching vibrations were present in the IR-spectrum.

EXAMPLE 4

Treatment of Aerosil 200 with Tri(2,3-epoxy-1-propyl) orthoformate =Orthoformic Acid Glycidylester= Triglycidylorthoformate Aerosil 200 was dried at 120° C./10$^{-2}$ mbar for 1 hour, immersed into a 10% solution of said orthoester in CCl4, and stirred at room temperature for 3 hours. The reaction product was analyzed by means of IR- and $^{13}$C-solid-NMR-spectroscopy, as well as by means of TGA (Thermogravimetric Analysis). The portion of organic product on Aerosil 200 typically was about 3 to 5% by weight.

The central carbon atom of the orthoester had disappeared in all cases from the $^{13}$C-NMR-spectrum; only the signals of the corresponding epoxyalcohol were visible.

EXAMPLE 5

Polymerization 130 mg of dibenzoylperoxide (recrystallized from CHCl$_3$/MeOH) were dissolved in 100 ml of freshly distilled styrene and 20 ml of freshly distilled methacrylic acid.

Glass plates, silicon, silicon dioxide and Aerosil, which had been treated according to the directions of Example 2 with tri(ethylacryl)orthoformate, were dried at 10$^{-2}$ mbar and then reacted for 8 hours at 60° C. with a styrene/methacrylic acid/dibenzoylperoxide solution. The portion of organic product on Aerosil 200 was 15% by weight. This portion did not change even after washing for 3 days with tetrahydrofuran, chloroform, carbon tetrachloride, dimethylsulfoxide or toluene. In the IR-spectrum signals of acid groups and phenyl rings could be identified.

EXAMPLE 6

The results of the measurements of the boundary and contact angles for water on various substrates immediately after the treatment with the stated orthoesters and/or after treatment of the treated surfaces with various solvents in an ultrasonic bath are compiled hereafter.

"Si(300AOx)" stands for a silicon layer having a surface layer of silicon dioxide of a thickness of 300 A.

The extracting agents are abbreviated as follows:

| | |
|---|---|
| $CCl_4$ | Carbon tetrachloride = tetrachloromethane |
| EtOH | Ethanol |
| THF | Tetrahydrofuran = tetramethyleneoxide |
| DMSO | Dimethylsulfoxide |
| $H_2O$ | Water |

6.1 Trimethylorthoformate = orthoformic acid methylester = trimethoxymethane

| Extraction | | Glass | Quartz | Si(300ÅOx) | Silicon |
|---|---|---|---|---|---|
| $CCl_4$ | 15 minutes | 44° | 57° | 62° | 69° |
| $CCl_4$ | 15 hours | 44° | 55° | 75° | 75° |
| EtOH | 15 minutes | 32° | 36° | 50° | 62° |
| EtOH | 3 hours | 38° | 34° | 47° | 64° |
| THF | 15 minutes | 45° | 41° | 51° | 67° |
| Untreated | | 8° | 14° | 46° | 42 ... 70° |

6.2 Triethylorthoformate = orthoformic acid ethylester = triethoxymethane

| Extraction | | Glass | Quartz | Si(300ÅOx) | Silicon |
|---|---|---|---|---|---|
| Unextracted | | 50° | 47° | 72° | 78° |
| $CCl_4$ | 15 min | 60° | 64° | 75° | 82° |
| $CCl_4$ | 15 h | 60° | 50° | 70° | 78° |
| EtOH | 15 min | 50° | 47° | 70° | 78° |
| EtOH | 15 h | 49° | 46° | 68° | 78° |
| THF | 15 min | 49° | 46° | 68° | 78° |
| Acetone | 15 min | 48° | 46° | 67° | 78° |
| DMSO | 15 min | 49° | 45° | 68° | 80° |
| $H_2O$ | 15 min | 50° | 44° | 62° | 78° |
| Untreated | | 8° | 14° | 46° | 42 ... 70° |

6.3 Tributylorthoformate = orthoformic acid butylester = tributoxymethane

| Extraction | | Glass | Quartz | Si(300ÅOx) | Silicon |
|---|---|---|---|---|---|
| Unextracted | | 70° | 53° | 78° | 93° |
| $CCl_4$ | 15 minutes | 70° | 58° | 78° | 93° |
| $CCl_4$ | 15 hours | 59° | 58° | 77° | 90° |
| EtOH | 15 minutes | 49° | 30° | 48° | 91° |
| DMSO | 15 minutes | 48° | 32° | 35° | 85° |
| $H_2O$ | 15 minutes | 42° | 30° | 33° | 90° |
| Untreated | | 8° | 14° | 46° | 42 ... 70° |

6.4 Triallylorthoformate = orthoformic acid allylester = triallyloxymethane

| Extraction | | Glass | Quartz | Si(300ÅOx) | Silicon |
|---|---|---|---|---|---|
| $CCl_4$ | 15 min | 45° | 50° | 66° | 93° |
| $CCl_4$ | 15 h | 46° | 47° | 67° | 93° |
| EtOH | 15 min | 48° | 43° | 66° | 93° |
| THF | 15 min | 46° | 45° | 64° | 90° |
| Acetone | 15 min | 46° | 42° | 62° | 90° |
| DMSO | 15 min | 44° | 44° | 63° | 90° |
| $H_2O$ | 15 min | 39° | 30° | 49° | 87° |
| Untreated | | 8° | 14° | 46° | 42 ... 70° |

These examples show that the compounds applied to the surfaces by means of orthoesters, acetals or ketals are not only very resistant to extraction but that the boundary or contact angle in some cases is even increased and thus the wettability is reduced. This is due to the fact that the solvents wash away adsorbed polar compounds from the surface.

EXAMPLE 7

Shear Tension Test Following DIN 54451

Adhesive: BETASEAL® HV-3 (registered Trade Mark of Gurit-Essex AG, CH-8807 Freienbach)

Adhesive area: 25×10 mm

Hight of adhesive strand: 2 mm

Bonded materials: electrophoretically primed sheet metal 100×25×1 mm; and Glass 100×25×5 mm A=untreated B=treated with BETASEAL® WIPE VP 04604 (registered Trade Mark of Gurit-Essex AG, CH-8807 Freienbach)

C=treated according to Example 4

Hardening: 7 days at 23° C./50% realtive humidity

| | A | B | C |
|---|---|---|---|
| Combined tension and shear resistance [N/mm$^2$] | 1.1 | 6.2 | 6.3 |
| Kind of fracture | adhesive | cohesive | cohesive |

Aging: 7 days at 70° C./100% relative humidity+1 day at −20° C.

| | A | B | C |
|---|---|---|---|
| Combined tension and shear resistance [N/mm$^2$] | 0.9 | 3.5 | 5.1 |
| Kind of fracture | adhesive | 80% cohesive | cohesive |

EXAMPLE 8

Heat Resistance of the Surface Modification

The desorption temperatures of various alcohols adsorbed on Aerosil 200, the surface of which was modified according to Example 2 by triethylorthoformate, were analyzed by means of TGA (Thermogravimetric Analysis) under nitrogen. The results are compiled in the following Table.

| | Desorption temperature [°C.] | Loss in weight [%] |
|---|---|---|
| Methanol | 485 | 1.6 |
| Ethanol | 570 | 2.0 |
| Butanol | 550 | 1.8 |
| Allylalcohol | 550 | 2.0 |
| 2-Hydroxyacrylate | 430 | 2.0 |
| Phenol | 195 | 2.8 |

EXAMPLE 9

Stability of Surface Modification Against Water

It was tried to substitute ethanol which was adsorbed on Aerosil 200, the surface of which had been modified according to Example 2 by triethylorthoformate, by water. For this purpose the product was contaced with water in various ways:

Desorption experiments:
a) 17 months stored in air at room temperature;
b) 1 month stored in an atmosphere saturated with water at room temperature;
c) 1 week stirred in water at room temperature;
d) 3 days boiled in water, about 100° C.;
e) 1 week extracted in a Kumagawa extractor, about 100° C.

When it was tried to bring the product into water, it turned up that the product no longer behaved hydrophilic as it did before treatment with the orthoester, but had taken a hydrophobic character. This resulted in a modified wettability. When it was tried to suspend it, it floated on the water. On the other hand, if the product was first introduced and the water was added afterwards, an air bubble was formed around the product. Only by vigorous stirring it was possible to supend the product. After this mechanical mixing it was no longer possible to determine whether or not the product was wetted.

No change with respect to adsorbed alcohol and water content could be determined by means of IR-spectroscopy in tests b) to e).

What is claimed is:

1. A silicon substrate or silicon dioxide substrate having at least one surface comprising alcohol or silylether moieties prepared by contacting a surface of said substrate with at least one orthoester.

2. A substrate according to claim 1, wherein said alcohol and silylether moieties comprise saturated aliphatic residues.

3. A substrate according to claim 1, wherein said alcohol or silylether moieties comprise unsaturated aliphatic residues.

4. A substrate according to claim 3, wherein said unsaturated alcohol or silylether moieties have been reacted with at least one unsaturated compound.

5. A substrate according to claim 4, wherein said unsaturated alcohol or silylether moieties have been reacted with at least one unsaturated compound without active hydrogen atoms.

6. A substrate according to claim 4, wherein said unsaturated alcohol or silylether moieties have been reacted with at least one unsaturated compound containing active hydrogen atoms.

7. A substrate according to claim 6, wherein said unsaturated alcohol or silylether moieties have been reacted with at least one compound of the general formula $$R-CH=C(R")-C(XR')=O$$

wherein:
R and R' independently from each other are a hydrogen atom or a substituent having at least one active hydrogen atom;
R" is a hydrogen atom or a substituent having at least one active hydrogen atom or an alkyl residue or CN; and
X is an oxygen or sulfur atom or the residue NH.

8. A substrate according to claim 6, wherein said unsaturated alcohol or silylether moieties have been reacted with acrylamide.

9. A substrate according to claim 6, wherein said unsaturated alcohol or silylether moieties have been reacted with at least one unsaturated compound of the general formula $$HY(CH_2)_n-C_6H_4-CH=CH_2$$

wherein:
n is an integer from 0 to 18; and
Y is an oxygen or sulfur atom or one of the residues NH, COO or $SO_3$.

10. A substrate according to claim 9, wherein said unsaturated alcohol or silylether moieties have been reacted with 4-hydroxystyrene or 4-aminostyrene.

11. A substrate according to claim 6, wherein said unsaturated alcohol or silylether moiety has been reacted with at least one unsaturated dicarbonic add or its anhydride.

12. A substrate according to claim 6, wherein said unsaturated alcohol or silylether moiety has been reacted with at least one epoxyacrylate or epoxymethacrylate.

13. A substrate according to claim 1, wherein said substrate comprises a silicate filler.

14. A substrate according to claim 1, wherein said substrate comprises silicate fibers.

15. A substrate according to claim 1, wherein said substrate is a flat glass.

16. A substrate according to claim 1, wherein said substrate is a silicon wafer.

17. A substrate according to claim 1, wherein said substrate is an aerogel glass.

18. A method of treating a silicon substrate or silicon dioxide substrate to improve the adhesion of organic compositions thereto, comprising contacting a surface of said substrate with at least one orthoester.

19. The method of claim 18, wherein said substrate surface is contacted with an orthoester having a saturated alcohol moiety.

20. The method of claim 18, wherein said substrate surface is contacted with an orthoester having an unsaturated alcohol moiety.

21. The method of claim 20, wherein said substrate surface is further contacted with at least one unsaturated compound other than an orthoester.

22. The method of claim 21, wherein said unsaturated compound other than an orthoester is an unsaturated compound without active hydrogen atoms.

23. The method of claim 21, wherein said unsaturated compound other than an orthoester is an unsaturated compound having active hydrogen atoms.

24. The method of claim 23 wherein said unsaturated compound having active hydrogen atoms is a compound of the general formula $$R-CH=C(R")-C(XR')=O$$

wherein:
R and R' independently from each other are a hydrogen atom or a substituent having at least one active hydrogen atom;
R" is a hydrogen atom or a substituent having at least one active hydrogen atom or an alkyl residue or CN; and
X is an oxygen or sulfur atom or the residue NH.

25. The method of claim 23, wherein said unsaturated compound having active hydrogen atoms is acrylamide.

26. The method of claim 23, wherein said unsaturated compound having active hydrogen atoms is a compound of the general formula $$HY(CH_2)_n-C_6H_4-CH=CH_2$$

wherein:
n is an integer from 0 to 18; and

Y is an oxygen or sulfur atom or one of the residues NH, COO or SO$_3$.

27. The method of claim 26, wherein said unsaturated compound having active hydrogen atoms is 4-hydroxystyrene or 4-aminostyrene.

28. The method of claim 23, wherein said unsaturated compound having active hydrogen atoms is a dicarbonic acid or its anhydride.

29. The method of claim 23, wherein said unsaturated compound having active hydrogen atoms is an epoxyacrylate or epoxymethacrylate.

30. A substrate according to claim 2 wherein said saturated aliphatic residues are residues of methanol, ethanol, propanol or butanol.

31. A substrate according to claim 1 wherein said alcohol or silylether moieties comprise glycidyl alcohol moieties or glycidyl silylether moieties.

32. A substrate according to claim 3 wherein said unsaturated aliphatic residues are residues of allyl alcohol or 2-hydroxyethyl acrylate.

33. A substrate according to claim 5 wherein said unsaturated compound without active hydrogen atoms is selected from the group consisting of compounds having at least one olefinic double bond, alkylacrylates, alkylmethacrylates, styrene and acrylonitrile.

34. A substrate according to claim 7 wherein said unsaturated alcohol or silylether moieties have been reacted with at least one unsaturated compound selected from the group consisting of acrylic acid, 2-hydroxyethylacrylate, 4-hydroxybutylacrylate, 2,3-dihydroxypropylacrylate, 2,3-dihydroxypropylmethacrylate, and hydroxypropylmethacrylate.

35. A substrate according to claim 11, wherein said unsaturated alcohol or silylether moiety has been reacted with maleic acid or maleic anhydride.

36. A substrate according to claim 12, wherein said unsaturated alcohol or silylether moiety has been reacted with 2,3-epoxypropylacrylate or 2,3-epoxypropylmethacrylate.

37. A substrate according to claim 13, wherein said substrate is selected from the group consisting of pyrogenic silicic acid, precipitated silicic acid, silica gel, quartz powder and glass powder.

38. A substrate according to claim 14, wherein said substrate is selected from the group consisting of glass fibers, glass textiles, glass wool, and rock wool.

39. A substrate according to claim 15, wherein said substrate is selected from the group consisting of a window glass composite, insulating glass system, optical glass, and glass membrane.

40. A substrate according to claim 16, wherein said silicon wafer is an oxidized wafer.

41. The method of claim 19, wherein said saturated alcohol moiety comprises a saturated aliphatic residue.

42. The method of claim 41, wherein said saturated aliphatic residue is derived from methanol, ethanol, propanol or butanol.

43. The method of claim 18, wherein said substrate surface is contacted with an orthoester having an alcohol moiety derived from a glycidyl alcohol.

44. The method of claim 20, wherein said unsaturated alcohol moiety comprises an unsaturated aliphatic residue.

45. The method of claim 44, wherein said unsaturated aliphatic residue is derived from allyl alcohol or 2-hydroxyethylacrylate.

46. The method of claim 21, wherein said unsaturated compound other than an orthoester is selected from the group consisting of alkylacrylates, alkylmethacrylates, styrene and acrylonitrile.

47. The method of claim 24, wherein said unsaturated compound having active hydrogen atoms is selected from the group consisting of acrylic acid, 2-hydroxyethylacrylate, 4-hydroxybutylacrylate, 2,3-dihydroxypropyl-acrylate, 2,3-dihydroxypropylmethylacrylate and hydroxypropylmethacrylate.

48. The method of claim 28, wherein said unsaturated compound having active hydrogen atoms is maleic acid or maleic anhydride.

49. The method of claim 29, wherein said unsaturated compound having active hydrogen atoms is 2,3-epoxypropylacrylate or 2,3-epoxypropylmethacrylate.

50. A method for improving the adhesion of an organic composition to the surface of a silicon or silicon dioxide substrate, comprising:

(1) first, contacting said surface of said substrate with an orthoester; and (2) second, contacting said substrate surface with said organic composition or precursor thereof.

51. The method of claim 50, wherein said orthoester is selected from compounds of the general formula R$^1$—C[OR$^2$]$_3$, wherein:

R$^1$ is hydrogen or an alkyl group having 1 to 4 carbon atoms and

R$^2$ is an alkyl group having 1 to 4 carbon atoms or an allyl group.

52. The method of claim 50, wherein said orthoester is selected from compounds of the formula R$^1$C[OR$^2$—O—CO—CH=CH$_2$]$_3$, wherein:

R$^1$ is hydrogen or an organic residue; and

R$^2$ is (CH$_2$)$_n$ where n is an integer from 1–18.

53. The method of claim 50, wherein said orthoester is selected from compounds of the general formula

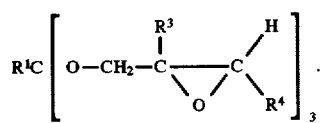

wherein:

R$^1$ is hydrogen or an organic residue;

R$^3$ is hydrogen or an alkyl group of 1 to 6 carbon atoms, and

R$^4$ is hydrogen, an alkyl group or a phenyl group.

54. The method of claim 52, wherein said organic composition precursor is selected from the group consisting of monomers having at least one olefinic double bond, alkylacrylates, alkylmethacrylates, styrene, acrylonitrile, compounds of the general formula

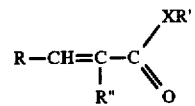

wherein

R and R' independently from each other are a hydrogen atom or a substituent having at least one active hydrogen atom;

R" is a hydrogen atom, a substituent having at least one active hydrogen atom, an alkyl residue, or CN; and X is an oxygen or sulfur atom, or the residue NH, compounds of the general formula

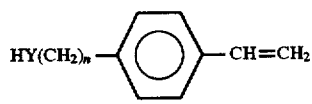

wherein:

n is an integer from 0 to 18; and

Y is an oxygen or sulfur atom or one of the residues NH, COO or $SO_3$;

unsaturated dicarbonic acids, unsaturated dicarbonic acid anhydrides, epoxyacrylates and epoxymethacrylates.

55. The method of claim 54, wherein said organic composition precursor is selected from the group consisting of acrylic acid, 2-hydroxyethylacrylate, 4-hydroxybutylacrylate, 2,3-dihydroxypropylacrylate, 2,3-dihydroxypropylmethacrylate, hydroxypropylmethacrylate, acrylamide, 4-hydroxystyrene, 4-aminostyrene, maleic acid, maleic anhydride 2,3-epoxypropylacrylate, and 2,3-epoxypropylmethacrylate.

56. The method of claim 55, wherein said orthoester is tri(ethylacrylate)orthoformate.

57. A silicon substrate or silicon dioxide substrate prepared by the method of claim 43.

58. A silicon substrate or silicon dioxide substrate prepared by the method of claim 56.

59. A silicon substrate or silicon dioxide substrate prepared by the method of claim 53.

60. A silicon substrate or silicon dioxide substrate prepared by the method of claim 54.

61. A silicon substrate or silicon dioxide substrate prepared by the method of claim 55.

62. Ortoesters of the general formula

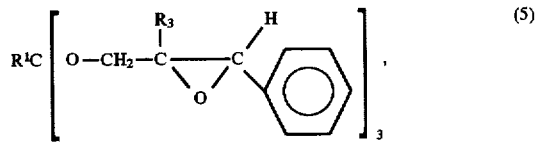

wherein:

$R^1$ is hydrogen or an organic residue; and $R^3$ is hydrogen or a methyl group.

* * * * *